US Patent [19] Bonucci

[11] 3,971,161
[45] July 27, 1976

[54] PRODUCTION OF HYBRID SWEET CORN
[75] Inventor: Peter A. Bonucci, Northfield, Minn.
[73] Assignee: Northrup, King & Co., Minneapolis, Minn.
[22] Filed: May 27, 1975
[21] Appl. No.: 580,963

[52] U.S. Cl. .................................................. 47/58
[51] Int. Cl.² ......................................... A01H 1/02
[58] Field of Search ........................................ 47/58

[56] References Cited
UNITED STATES PATENTS

| | | | |
|---|---|---|---|
| 2,753,663 | 7/1956 | Jones | 47/58 |
| 3,570,181 | 3/1971 | Davis | 47/58 |
| 3,710,511 | 1/1973 | Patterson | 47/58 |
| 3,903,645 | 9/1975 | Bradner | 47/58 |

Primary Examiner—Robert E. Bagwill
Attorney, Agent, or Firm—Thomas M. Meshbesher

[57] ABSTRACT

The sugar content of sweet corn can be increased without seriously reducing the water soluble polysaccharide (WSP) by using the shrunken$_2$ ($sh_2$) gene. Combining a sweet corn which is a homozygous sugary$_1$ ($su_1$) inbred with a sweet corn (homozygous $su_1$ $sh_2$) inbred will result in heterozygous hybrid that has approximately 50% more sucrose, 33% more total sugars and a WSP (water soluble polysaccharide) level near that of sweet corn) homozygous $su_1$). The high WSP and sucrose levels are particularly desirable in food processing industries such as the canning and freezing industries.

4 Claims, No Drawings

PRODUCTION OF HYBRID SWEET CORN

FIELD OF THE INVENTION

This invention relates to a method for producing hybrid sweet corn seeds in commercial quantities. An aspect of this invention relates to a method for increasing the sugar content of sweet corn without seriously reducing the water soluble polysaccharide content. Another aspect of this invention relates to a method for producing seeds which provide a sweet corn suitable for processing with a minimal amount of extraneous sweeteners.

DESCRIPTION OF THE PRIOR ART

The various species of corn (i.e. maize) have widely differing uses because of, inter alia, the widely differing carbohydrate content of the kernels. For example, field corn can be a good livestock feed, but is not well suited for human consumption. Sweet corn, on the other hand, can be highly palatable to humans, due to its unusually high content of water soluble polysaccharide, commonly abbreviated WSP. It is the WSP which gives the sweet corn kernels their smooth, creamy characteristics which contrast sharply with the gritty, excessively starchy effect experienced when eating corn which is too low in WSP. Thus, while the sugar content of normal sweet corn is also somewhat higher than that of field corn, it is actually the high WSP level of sweet corn which appears to be the factor most essential to the taste commonly associated with what American consumers refer to as "corn".

In the industrial practice of processing (e.g. canning and freezing) vegetables, on the other hand, both the WSP level and the sugar level can be important. In a typical canning process, for example, the kernels are removed from the ears of sweet corn and the resulting mass of detached kernels (or "cut", as it is sometimes called) is automatically packaged in cans along with a watery liquor. Most commonly, extraneous natural sweeteners such as sucrose or honey are added to the liquor to increase the natural sweetness of the sweet corn. It is the experience of most canneries that the normal or natural level of sweetness in sweet corn is not high enough for canning. A hybrid corn which was very high in both sugars and WSP would be an improvement over normal sweet corn, at least from the standpoint of typical processing operations.

Unfortunately, most attempts to produce hybrids with unusually high sugar (e.g. sucrose) content have resulted in a product which is far below normal sweet corn in WSP content. Among the most interesting work in high sugar-content corn research has been with a mutant gene known as shrunken-2, commonly written "$sh_2$". Including the $sh_2$ gene in the genetic makeup of corn does increase sweetness, but it also lowers WSP content and causes problems due to the reduced endosperm and lowered starch levels, resulting in a lightweight, easily damaged seed. Germination of these light-weight seeds can be a problem both in inbred production and hybrid stands. To improve vigor and germination, dent corn (a species of field corn) has been used as the background for the $sh_2$ gene. However, the dominant dent corn genes can necessitate isolation of the hybrid from both field and sweet corn. Any foreign pollen can cause all the kernels to be dent corn in character.

For a review of the effects of genetic interactions of the $sh_2$ gene with other genes (e.g. the "sugary-1" gene, $su_1$), with particular emphasis on investigating carbohydrate composition of the kernels, see:

Rosenbrook and Andrew, Crop Science 11:536–538 (1971).
Holder, Glover, and Shannon, Crop Science 14:647–648 (1974).
Holder, Glover, and Shannon, Crop Science 14:643–646 (1974).

The applicant is also aware of a report (apparently unpublished) to the members of the NE-66 Technical Committee from W. C. Galinat, Sub-committee Chairman. The report was dated Dec. 3, 1973, and its subject was "Evolution and Morphology". Among the topics discussed in the report is some work done on so-called "Ultrasweet" or "Supersweet" sweet corn based on the combination of the recessive gene shrunken-2 ($sh_2$) on chromosome 3 with the dominant starchy-1 ($Su_1$) on chromosome 4. The shrunken-sugary combination ($sh_2su_1$) is also discussed. The $sh_2su_1$ combination was said to be "defective to the point of being nearly lethal and impossible to produce except in a background of pseudo starchy-sugary." It was further reported that the combination of $sh_2su_1$ can be produced commercially by having the 7th chromosome of Tripsacum ($Tr_7$), which carries the $Su_1$ allele, "present as an extra pair in the seed parent". The report then goes on to describe a hybrid produced by the cross $sh_2su_1Tr_7 \times sh_2su_1$.

In short, as presently understood by the applicant, this December 1973 NE-66 report suggests using $su_1$ and $sh_2$ in a homozygous condition.

SUMMARY OF THE INVENTION

It has now been found that hybrid sweet corn seeds which can provide a hybrid corn which is very high in both sugars and WSP (water soluble polysaccharide) by crossing sweet corn (homozygous $su_1$, genotypically represented as $su_1su_1Sh_2Sh_2$) with sugary-shrunken corn (homozygous $su_1sh_2$, genotypically represented as $su_1su_1sh_2sh_2$), thereby obtaining $F_1$ ears of corn which are heterozygous and are genotypically represented as: $su_1su_1Sh_2sh_2$. When the heterozygous hybrid is subsequently planted, the resulting $F_2$ ears of corn have phenotypically uniform kernels, but only about 25% of the kernels can be genotypically represented as $su_1su_1su_1sh_2sh_2sh_2$. The balance of the kernels (about 75%) are normal sweet corn kernels.

From the standpoint of canning the "cut" from the $F_2$ ears, the system which provides the aforementioned 75%/25% kernel segregation is particularly advantageous. The heterozygous hybrid is a compromise between the present $su_1$ and $sh_2$ hybrids now available. Compared to normal sweet corn, it would appear to increase the sucrose content by approximately 50% and total sugars by approximately 30%, while maintaining WSP at 80%. Compared with $sh_2$ hybrids, it has approximately 75% of the sucrose and approximately 75% of the total sugars, but WSP appears to be increased by a factor of more than 40. Since normal appearing sweet corn kernels are planted, germination is no more of a problem than with sweet corn. Cross pollination with sweet corn results in sweet corn kernels.

In the preferred method for producing hybrid sweet corn seeds in accordance with this invention, the parents are (1) normal sweet corn inbred, homozygous for $su_1$, and (2) shrunken-sugary sweet corn inbred, homozygous for $su_1sh_2$. Parents (1) and (2) are planted in alternate rows of 1:2, 1:4, or any other ratio that will provide optimum cross pollination when one of the two parents is detasseled. As a result, the $F_1$ ears of the detasseled row provide the desired hybrid sweet corn seeds.

Outlined in a step-wise fashion, the preferred method is as follows:

a. At least one row of sweet corn (homozygous $su_1$) is planted.
b. At least one row of sugary-shrunken corn (homozygous $su_1sh_2$) is planted near the row of sweet corn, close enough for cross-breeding to occur if one of the aforementioned (a) or (b) rows of resulting plants is detasseled.
c. A conventional detasseling is then carried out on one of the two rows of plants resulting from steps (a) and (b), whereby the detasseled row can serve as a female parent and the row with tassels left intact can serve as a male parent.
d. As a result of the preceding steps, the $F_1$ ears of corn of the detasseled row, when harvested, will provide commercial quantities of hybrid sweet corn seeds of the heterozygous genotype which can be represented as $su_1su_1Sh_2sh_2$.

DETAILED DESCRIPTION

The parents for the heterozygous $F_1$ ears of this invention are well known, have been experimented with extensively, and are described in the literature. See for example, the *Crop Science* articles cited previously.

Although normal sweet corn can be used as either the male of female parent, it is preferred to use normal sweet corn as the female parent. The male parent (i.e. still tasseled parent), in this case, is a (homozygous sugary-shrunken) corn with a sweet corn background. Accordingly, using the notations $su_1su_1sh_2sh_2$ to represent the sugary-shrunken parent and $su_1su_1Sh_2Sh_2$ to represent the normal sweet corn parent, the system or method of producing commercial quantities of heterozygous $F_1$ seed can be schematically represented as follows:

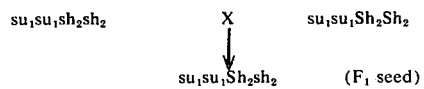

$$su_1su_1sh_2sh_2 \quad \text{X} \quad su_1su_1Sh_2Sh_2$$
$$\downarrow$$
$$su_1su_1Sh_2sh_2 \quad (F_1 \text{ seed})$$

The method of producing the seed, on other words, is the four-step preferred method described previously. The $F_1$ is normal sweet corn seed; however, due to the previously described heterozygosity, planting and field pollination produces $F_2$ ears characterized by a 3:1 segregation of normal kernels to shrunken ($sh_2$) kernels; phen typically all kernels appear the same, however.

Schematically represented, the genetic composition of the 3N endosperm of the kernels is an follows:

| | Genotype | Ratio |
|---|---|---|
| Normal Sweet Corn | $su_1su_1su_1Sh_2Sh_2Sh_2$ | 1 |
| | $su_1su_1su_1Sh_2Sh_2sh_2$ | 1 |
| | $su_1su_1su_1Sh_2sh_2sh_2$ | 1 |
| | $su_1su_1su_1sh_2sh_2sh_2$ | 1 |

The $sh_2$ kernels increase the average sugar content of the "cut", while the normal sweet corn kernels maintain the average WSP at a high level. When the consumer samples a spoonful of $F_2$ kernels, he tastes only the effects provided by these averages. He does not sense that some kernels are relatively lower in WSP and relatively higher in sucrose of that other kernels are relatively lower in sucrose and relatively higher in WSP. Actual experience in canning processes indicates that the "cut" can be successfully processed. In a few instances, discoloration of the $su_1su_1su_1sh_2sh_2sh_2$ kernels was noted, but this color change, if it occurs, does not appear to adversely affect other desired properties.

The combined effect of 25% high-sugar $F_2$ kernels with 75% high-WSP $F_2$ kernels can thus be very favorable for processing of the "cut". The average content of sucrose, total sugar (sucrose + fructose + glucose), and WSP (water soluble polysaccharide), in the $F_2$ "cut", on a dry weight basis is as follows:

| | Wt. %, Compared to Normal Sweet Corn (S/C), i.e. S/C = 100 |
|---|---|
| Sucrose:; | >150 |
| Total Sugar: | >130 |
| WSP: | >75 |
| | Wt. %, Compared to Sweet Corn (S/C) Super-sweet hybrids, i.e. S/C super-sweet = 100 |
| Sucrose: | >45 |
| Total Sugar: | >50 |
| WSP: | >400 |
| | Wt. %, Compared to Super-sweet Corn with Normal (field) Corn Background i.e. Normal sweet corn = 100 |
| Sucrose: | >70 |
| Total Sugar: | >70 |
| WSP: | >4000 |

Published data are available for the carbohydrate content of $F_2$ kernels obtained from normal (field) corn, sweet corn, super-sweet corn with a normal (field) corn background, and super-sweet corn with a sweet corn background, as well as the individual $F_2$ genotypes $su_1su_1su_1Sh_2Sh_2Sh_2$, $su_1su_1su_1Sh_2Sh_2sh_2$, $su_1su_1su_1Sh_2sh_2sh_2$, and $su_1su_1su_1sh_2sh_2sh_2$ (hereinafter referred to as the "four genotypes").

The following table summarizes averages of this published data.

DRY WEIGHT OF VARIOUS CARBOHYDRATES
21 DAYS AFTER POLLINATION (70–76% moisture)

| Genotype | Sucrose | Dry Weight, % Total Sugar | WSP | Starch |
|---|---|---|---|---|
| Normal $su_1su_1Sh_2Sh_2$ | 7.3 | 10.5 | 0.55 | 47.0 |
| Sweet Corn $su_1su_1Sh_2Sh_2$ | 12.5 | 18.1 | 36.6 | 18.3 |
| Normal Super-sweet $Su_1Su_1sh_2sh_2$ | 26.0 | 32.7 | 0.67 | 17.3 |
| Sweet Corn Super-sweet $su_1su_1sh_2sh_2$ | 39.8 | 44.3 | 7.1 | 2.8 |
| Average of "Four genotypes", in 1:1:1:1 ratio | 19.3 | 24.7 | 29.2 | 14.4 |

What is claimed is:

1. A method for producing hybrid sweet corn seeds in commercial quantities comprising the steps of:

a. planting a row of normal sweet corn, homozygous for $su_1$, wherein said sweet corn can be genotypically represented as follows: $su_1su_1Sh_2Sh_2$;
b. planting a row of sugary-shrunken corn in cross-breeding proximity to said row of normal sweet corn, wherein said sugary-shrunken corn can be genotypically represented as follows: $su_1su_1sh_2sh_2$;

c. detasseling one of the two rows of plants resulting from steps (a) and (b), whereby the detasseled row serves as a female parent and the row with tassels remaining intact serves as a male parent;

d. harvesting the $F_1$ ears of corn of the detasseled row to obtain commercial quantities of hybrid sweet corn from said ears of corn, said hybrid sweet corn seeds obtained from said $F_1$ ears of corn being heterozygous and genotypically represented as: $su_1su_1Sh_2Sh_2$.

2. A method according to claim 1 wherein said hybrid sweet corn seeds are subsequently planted to obtain $F_2$ ears of corn each of which has phenotypically uniform kernels about 75% of which are normal sweet corn kernels, and about 25% of which can be genotypically represented as follows: $su_1su_1su_1sh_2sh_2sh_2$.

3. A method according to claim 2 wherein said kernels are mechanically removed from said $F_2$ ears and canned to provide a canned sweet corn product.

4. A method according to claim 2 wherein the average carbohydrate content for all the kernels of each $F_2$ ear, on a dry weight basis, is as follows:

at least about 150% of the sucrose content in normal sweet corn kernels, at least about 130% of the total sugar content in normal sweet corn kernels, at least about 75% of the water soluble polysaccharide content of sweet corn kernels, at least 45% of the sucrose content in sugary-shrunken hybrid corn kernels, at least 50% of the total sugar content in sugary-shrunken hybrid corn kernels, and at least about 400% of the water soluble polysaccharide content of the sugary-shrunken hybrid corn kernels.

* * * * *